United States Patent [19]

Hart et al.

[11] Patent Number: 5,308,336
[45] Date of Patent: May 3, 1994

[54] SEAL PROTECTION MECHANISM

[75] Inventors: Charles C. Hart, Huntington Beach; Mark A. Ritchart, Murrieta, both of Calif.

[73] Assignee: Applied Medical Resources, Laguna Hills, Calif.

[21] Appl. No.: 952,300

[22] Filed: Sep. 28, 1982

Related U.S. Application Data

[63] Continuation-in-part of Ser. No. 732,141, Jul. 18, 1992, Pat. No. 5,209,737.

[51] Int. Cl.⁵ .............................. A61M 5/178
[52] U.S. Cl. .................... 604/167; 604/256
[58] Field of Search ................. 604/167, 256

[56] References Cited

U.S. PATENT DOCUMENTS

| | | |
|---|---|---|
| 3,853,127 | 12/1974 | Spademan . |
| 3,994,287 | 11/1976 | Turp . |
| 4,240,211 | 12/1980 | Hosono ........................ 604/167 |
| 4,430,081 | 2/1984 | Timmermans . |
| 4,673,393 | 6/1987 | Suzuki . |
| 4,715,360 | 12/1987 | Akui et al. .................... 604/256 |
| 4,723,550 | 2/1988 | Bales . |
| 4,758,225 | 7/1988 | Cox et al. .................... 604/167 |
| 4,842,591 | 6/1989 | Luther . |
| 4,857,062 | 8/1989 | Russell . |
| 4,909,798 | 3/1990 | Fleischhacker . |
| 4,929,235 | 5/1990 | Merry et al. .................... 604/167 |
| 4,960,412 | 10/1990 | Fink . |
| 4,966,588 | 10/1990 | Rayman . |
| 5,104,383 | 4/1992 | Schichman ................... 604/167 |
| 5,127,626 | 7/1992 | Hilal et al. .................... 604/167 |
| 5,156,596 | 10/1992 | Balbierz et al. ............... 604/167 |
| 5,180,373 | 1/1993 | Green et al. ................... 604/167 |
| 5,197,955 | 3/1993 | Stephens et al. .............. 604/167 |

Primary Examiner—Paul J. Hirsch
Attorney, Agent, or Firm—Richard L. Myers

[57] ABSTRACT

An access device has an axis extending between a proximal end and an opposing distal end, and properties for facilitating introduction into the body of an instrument having a pointed distal tip. The device includes a housing having walls defining a channel extending through the device and a valve disposed in the housing across the channel and adapted to form a seal around the instrument. The valve includes inner portions defining an aperture to receive the instrument and outer portions extending radially outwardly of the inner portions. Means carried by the housing is positioned to be disposed between the instrument and at least the outer portion of the seal for isolating the seal from the pointed distal tip during insertion of the instrument.

24 Claims, 5 Drawing Sheets

SEAL PROTECTION MECHANISM

CROSS REFERENCE TO RELATED APPLICATIONS

This application is a continuation-in-part of U.S. patent application Ser. No. 07/732,141, filed on Jul. 18, 1992 and entitled Lever Actuated Septum Seal, now U.S. Pat. No. 5,209,737.

BACKGROUND OF THE INVENTION

1. Field of the Invention

This invention relates generally to trocars and more specifically to devices for protecting an septum seal within a trocar.

2. Discussion of the Prior Art

Laparoscopic surgery is conducted through trocars which extend across the abdominal wall and provide channels through which instruments such as scopes, retractors and staplers can be inserted to perform surgery in the abdominal cavity. As a part of this procedure, the abdomen is inflated with an insufflation gas to maintain the abdomen in a distended state. Valves are typically provided in the trocars to form seals around the instruments in order to prevent leakage of this insufflation gas. A variable diameter septum valve is of particular advantage for this purpose as it is able to conform to any size of instrument, regardless of its diameter, without increasing the friction or drag on the instrument. A variable diameter septum valve of this nature is disclosed and claimed by applicant in the parent application Ser. No. 07/732,141, filed on Jul. 18, 1992 and entitled Lever Actuated Septum Seal, now U.S. Pat. No. 5,209,737.

Variable diameter seals have a high degree of compliance which is of particular advantage in accommodating different sized of instruments. However, this compliance can present a problem if a particular instrument is bifurcated or is inserted off center. Under these circumstances, the sharp point of the instrument can localize forces along the side of the valve providing undesirable cupping and perhaps tearing of the seal. This can occur with any septum seal, although the highly compliant variable diameter seals appear to be most susceptible to damage.

SUMMARY OF THE INVENTION

In accordance with the present invention, a protection mechanism has the configuration of a funnel extending along the axis of the trocar. In one embodiment, this mechanism engages the instrument in an extended position but is movable with the instrument distally axially into close proximity with the septum valve. In this distal position, the mechanism extends between the instrument and at least the outer portions of the seal. In a preferred embodiment, the mechanism actually extends through an aperture in the seal as the instrument passes through an aperture. When forward pressure on the instrument ceases, the elastomeric characteristics of the seal radially compress the protection mechanism and tend to move it rearwardly to its initial proximal position. This movement can be assisted by a slight withdrawal of the instrument if necessary. With the protection mechanism disposed in the proximal position, the septum valve is free to form a seal with the instrument.

This seal mechanism is effective in trocars having any form of septum valve, although it is particularly valuable where the septum valve is highly compliant as is the case with a variable diameter seal. The lever arms which are normally associated with a variable diameter seal can actually assist in radially spreading the valve during insertion of the instrument, and in returning the mechanism to the proximal position when the instrument has been operatively positioned.

In one aspect the invention includes an access device having an axis extending between the proximal end and an opposing distal end, and properties facilitating introduction into the body of an instrument having a sharp distal tip. The device includes a housing having walls defining a channel and a septum valve disposed across the channel to form a seal with an instrument extending through the channel. The valve includes inner portions defining an aperture and outer portions extending radially outwardly of the inner portions. Means is disposed between the instrument and at least the outer portion of the seal for isolating the seal from the sharp distal tip of the instrument.

In another aspect of the invention, the valve includes lip portions defining a hole to receive the instrument and outer portions extending radially outwardly of the lip portions. Means is disposed between the instrument and at least the outer portions of the valve for funneling the sharp distal tip of the instrument toward the hole.

In an additional aspect of the invention, means is disposed proximally of the valve for prestressing the valve in response to insertion of the instrument. The prestressing means enlarges the hole of the valve prior to introduction of the instrument. In this aspect, means is provided for funneling the instrument toward the prestressed hole to avoid substantial contact between the valve and the instrument during insertion.

These and other features and advantages of the invention will be more apparent with a discussion of preferred embodiments and the best mode of the invention, taken in combination with the associated drawings.

DESCRIPTION OF PREFERRED EMBODIMENT AND BEST MODE OF THE INVENTION

Figure 1:
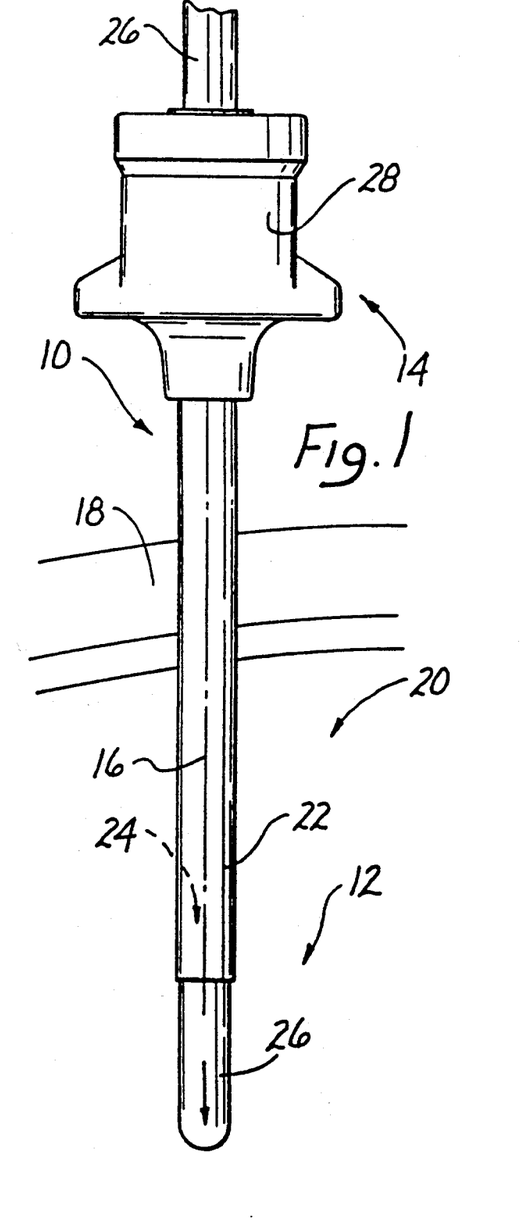
FIG. 1 is a side elevation of a trocar assembly operatively positioned to penetrate a tissue barrier.

A surgical trocar is illustrated in FIG. 1 and designated generally by the reference numeral 10. The trocar 10 is representative of any elongate access device having a distal end 12 and a proximal end 14. It is typically configured along a longitudinal axis 16 and is generally circular in radial cross-section.

It is the purpose of the trocar 10 to form a channel through a tissue barrier in order to provide access across the barrier into a body cavity. By way of example, the tissue barrier may include an abdominal wall 18 which defines an abdominal cavity 20. The trocar 10 typically includes an elongate tube or cannula 22 having a cylindrical configuration and a wall thickness which may be on the order of 0.015 or 0.030 inches. The cannula 22 has an interior bore or channel 24 which may have a diameter in a range between 5 and 12 millimeters. The trocar 10 is designed to pierce, cut, incise, or otherwise puncture the tissue barrier, such as the abdominal wall 18, and to leave the cannula 22 extending through the incision. An elongate surgical instrument 26 is representative of various cutters, clamps, traction devices, visualization devices, aspirators and irrigators as well as other types of instrument, which have different diameters. In operation, the instrument 26 is positioned through the channel 24 of the trocar 10 and manipulated to perform a particular surgical procedure within the cavity 20.

Figure 2:
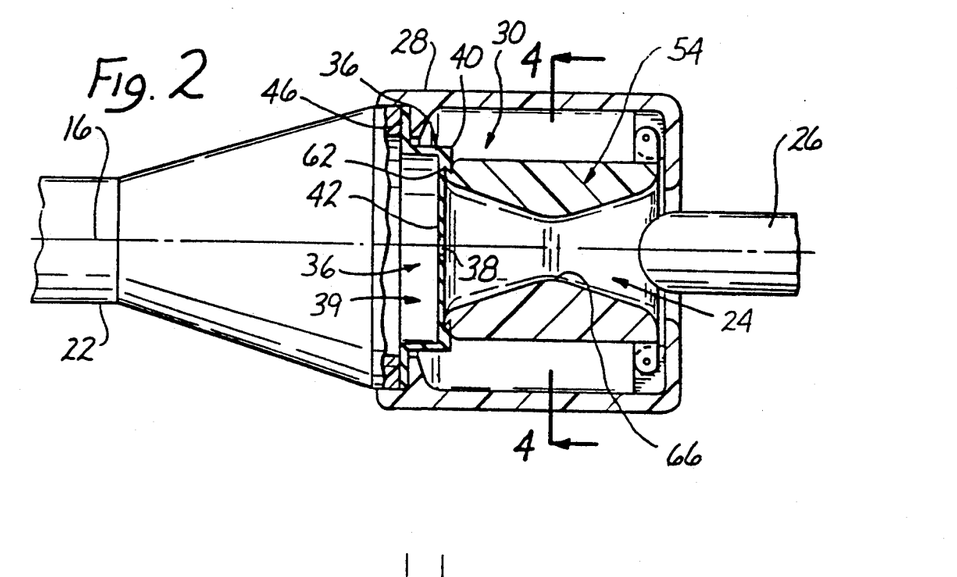
FIG. 2 is an axial cross-section view of the trocar, showing details of a variable diameter septum valve assembly prior to insertion of a surgical instrument therein.
Figure 3:
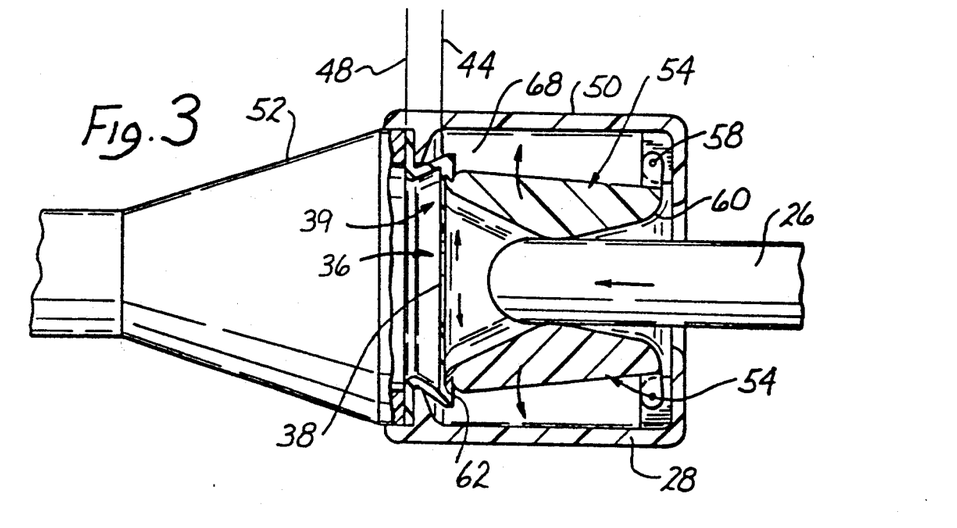
FIG. 3 is an axial cross-section view similar to that of FIG. 2, showing details of the same embodiment of the trocar valve assembly during insertion of the surgical instrument.
Figure 4:
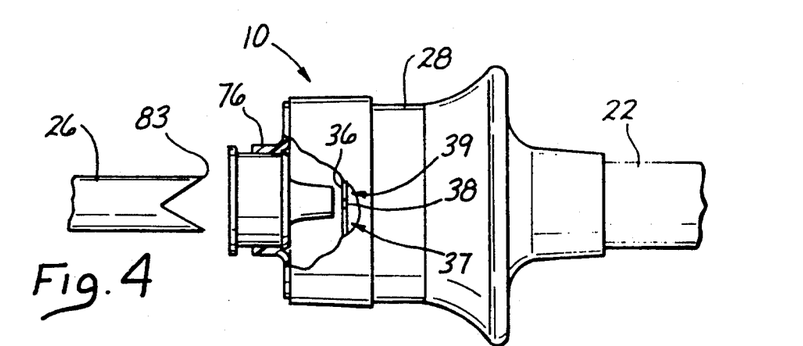
FIG. 4 is a side elevation view of a trocar extending across the abdominal wall and including one embodiment of a seal protection mechanism of the present invention.

The trocar 10 includes a valve housing 28 which encloses a valve mechanism 30 such as that shown in FIGS. 2-4. These figures illustrate the trocar 10 at a point in time after it has been inserted through the abdominal wall 18 leaving the cannula 22 to provide access to the abdominal cavity 20.

The valving mechanism 30 includes a septum valve 36, which is preferably molded from an elastomeric material such as C-flex ®, a low durometer polymer manufactured by Concept Polymer Technologies. This material is chosen for its high degree of compliance which makes it particularly adaptable to instruments having different diameters. Of course, other known elastomeric materials could be used instead to accomplish the objectives of the invention.

The valve 36, which is characterized as a septum valve, is deemed to include any valve which has properties for radially compressing against the outer surface of an instrument, such as the instrument 26. Included in this definition without limitation is the valve disclosed and claimed in applicant's U.S. Pat. No. 5,127,626, issued on Jul. 7, 1992, and entitled Apparatus for Sealing Around Members Extending Therethrough.

The septum valve 36 includes inner portions 37 which define a central orifice or aperture 38 that is preferably centered about the axis 16 of the trocar 10. The aperture 38 in a relaxed state has a cross-sectional area which, in one embodiment may be substantially zero, and in a different embodiment may be small, but greater than zero. The septum valve 36 also includes outer portions 39 which extend radially outwardly from the inner portions 37.

In the illustrated embodiment, the septum valve 36 also includes an annular flange or lip 40 which is preferably concentric with the aperture 38 and may be disposed in either the inner portions 37 or outer portions 39. The septum valve 36 in the illustrated embodiment also includes seating portions 46 which are clamped between the valve housing 28 and a transition housing 52.

A plurality of levers 54 are disposed outwardly of the elongate axis 16, in such a manner as to define a continuation of the channel 24. In a preferred embodiment, four such levers 54 are provided, but any number of levers could be employed, with suitable modifications in design.

Each lever 54 can be mounted on a pivot 58 at its proximal end 60, with the pivotal axis being transverse to the elongate axis 16. At least one tooth member 62 can be provided at a distal end 64 of each lever 54. This tooth member 62 is adapted to engage and interlock with the lip 40. In the illustrated embodiment, the lever teeth 62 collectively form a substantially circular tooth member which engages the circular lip 40 about it circumference. Between the pivot point 58 and the tooth member 62, each of the levers 54 extends radially inwardly to define a throat 66 of the channel 24. An open space 68 lies radially outwardly of both the levers 54 and the annular flange or lip 40, within the valve housing 28. This space 68 accommodates outward expansion of the levers 54 and the septum valve 36.

In operation, it may be desired to insert the surgical instrument 26 through the channel 24 and into the body cavity 18. To do so, the instrument 26 is first inserted into the valve housing 28 as shown in FIG. 3. The instrument 26 has a particular cross-sectional diameter which may vary according to the type of instrument, but it must be greater than the radial distance separating the levers 54 in order for the levers 54 to be actuated.

As the instrument 26 is pushed into the throat 66 of the channel 24, it pushes the levers 54 radially outwardly, thereby rotating the levers about their respective pivots 58. This moves the tooth members 62 of the lever 54 radially outwardly, as shown by the arrows 67 in FIG. 3. The engaging relationship between the lever teeth 62 and the lip 40 expands the lip radially outwardly thereby expanding the diameter of the aperture 38.

The leverage provided by the levers 54 is best illustrated again by reference to FIG. 3, where it can be seen that the lever arm for measuring the diameter of the instrument 26 is less than the lever arm for spreading the lip 40. The expansion of the lip 40 in turn stretches the inner portions 42 of the septum 36, causing the radial width of the aperture 38 to be expanded, as shown by the arrows 67. The aperture is preferably expanded to a cross-sectional diameter which is slightly smaller than the cross-sectional diameter of the instrument 26. This will enable the instrument 26 to pass easily through the aperture 8 while the valve 36 engages the instrument with a force sufficient to create a seal. With the valve 36 prestressed by the levers 54, this sealing force will not create significant frictional resistance between the instrument 26 and the septum 38. Such resistance is to be avoided since it not only opposes forward movement of the instrument 26, but also tends to tear the valve 38.

Of particular interest to the present invention is an embodiment illustrated in FIG. 4 wherein the trocar 10 is provided with a proximal end cap 74 which can be held in a snap fit relationship with the valve housing 28. This end cap 74 includes an annular flange 76 which extends axially proximally of the trocar 10. This flange 76 is adapted to receive a seal protector 81 which is of particular interest to the present invention.

The protector 81 is movable axially within the flange 76 between a proximal position illustrated in FIG. 4 and a distal position discussed in greater detail below. This protector 81 is particularly advantageous when the trocar 10 is used in conjunction with an instrument 26 having sharp points at its distal tip. Such an instrument 26 might include a clip applier having a bifurcated distal end with pointed tips 83.

Figure 5:
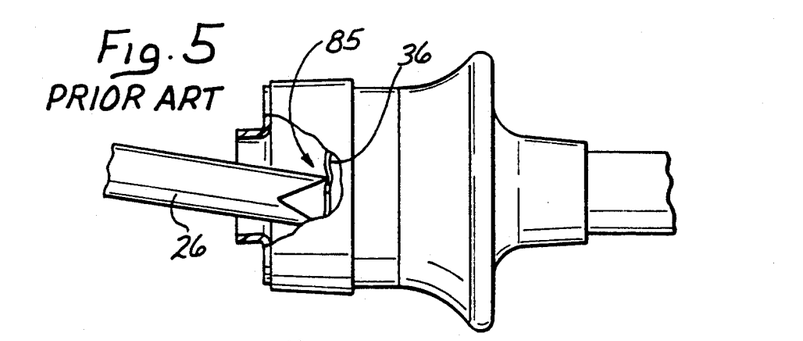
FIG. 5 is a side elevation view of a trocar of the prior art illustrating a cupping problem associated with some instruments.

Use of such an instrument 26 with previous trocars has been particularly damaging to the septum valves of the prior art as can be appreciated with reference to FIG. 5. When instruments having pointed tips have been inserted into the trocars of the prior art, the tips have sometimes engaged the septum valve outwardly from the central orifice or aperture. Preferably, the valve would spread radially under these conditions so that the instrument would eventually pass through the central aperture. However, in some cases, the valve 36 has been formed from sufficiently compliant material that it has tended to form a cup such as that shown generally at 85 in FIG. 5. When this happens, the localized pressure caused by the insertion forces has typically punctured or torn the septum 36.

Although cupping is most commonly associated with instrument having bifurcated tips, the problem can occur with any type of instrument having a pointed tip. Also, cupping can result with any type of septum valve although the highly compliant variable diameter valves, such as valve 36, previously discussed appear to be most susceptible.

It is the purpose of the seal protector 81 to isolate the outer portions 39 of the septum valve 36 from damaging contact with a pointed instrument tip, such as the tip 83. For the purposes of this discussion the inner portions 37 and outer portions 39 of the valve 36 are separated based on the response of a particular valve 36 to a pointed tip 83. If the tip 83 contacts the valve 36 at a point on the valve 36 where cupping would occur, this point is deemed to be within the outer portions 39. In contradistinction, if the pointed tip 83 of an instrument 26 contacts the valve 36 at a point on the valve which would not produce cupping, that point is deemed to be within the inner portions 37. Thus the inner portions 37 and outer portions 39 will vary for different septum valves 36 depending upon the shape and material of the valve 36 as well as the configuration of the tip 83 of the instrument 26. The compliance of the material forming the valve will be a primary consideration, but other physical characteristics of the valve 36 may also contribute to cupping at a particular point on the valve 36.

Figure 6:
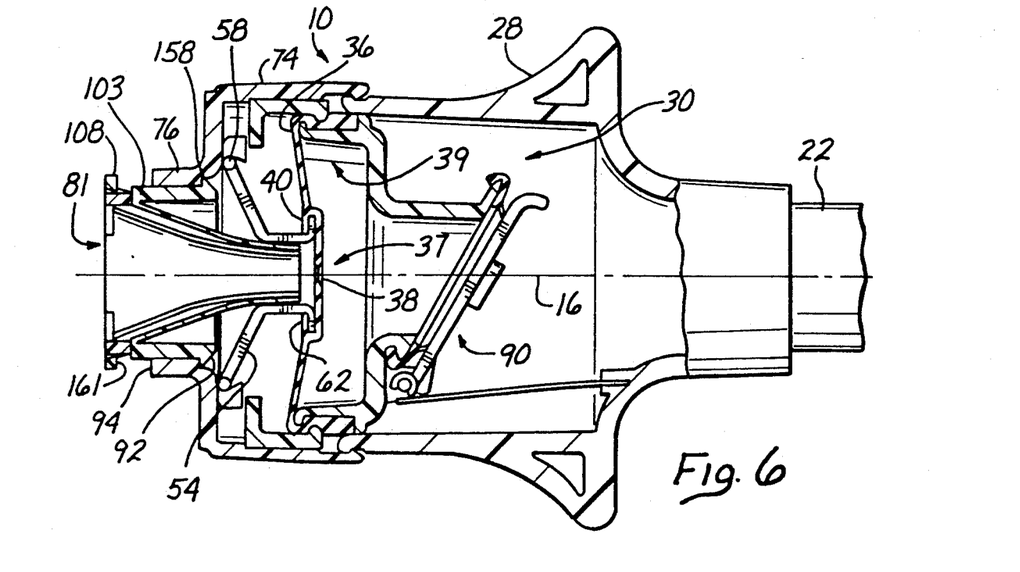
FIG. 6 is an axial cross-section view of a trocar and a further embodiment of the seal protection mechanism of the present invention.

The invention is illustrated in greater detail in FIG. 6 which differs from previously described embodiments in several respects. In the embodiment of FIG. 6, the valving mechanism 30 includes not only the septum valve 36 but also a flapper valve 90 which is of no particular interest to the present invention. Although the levers 54 are illustrated to have a more narrow configuration, they still pivot at the point 58 and include the tooth member 62. The septum valve 36 has a different configuration, but it also extends across the channel 24 and includes the inner portions 37 which define the aperture 38 and the outer portions 39 which form a seal with the housing 28. In this detailed view of FIG. 6, it is apparent that the annular flange 76 of the end cap 74 includes an inner shoulder and an outer surface 94.

Figures 9, 10, 11:
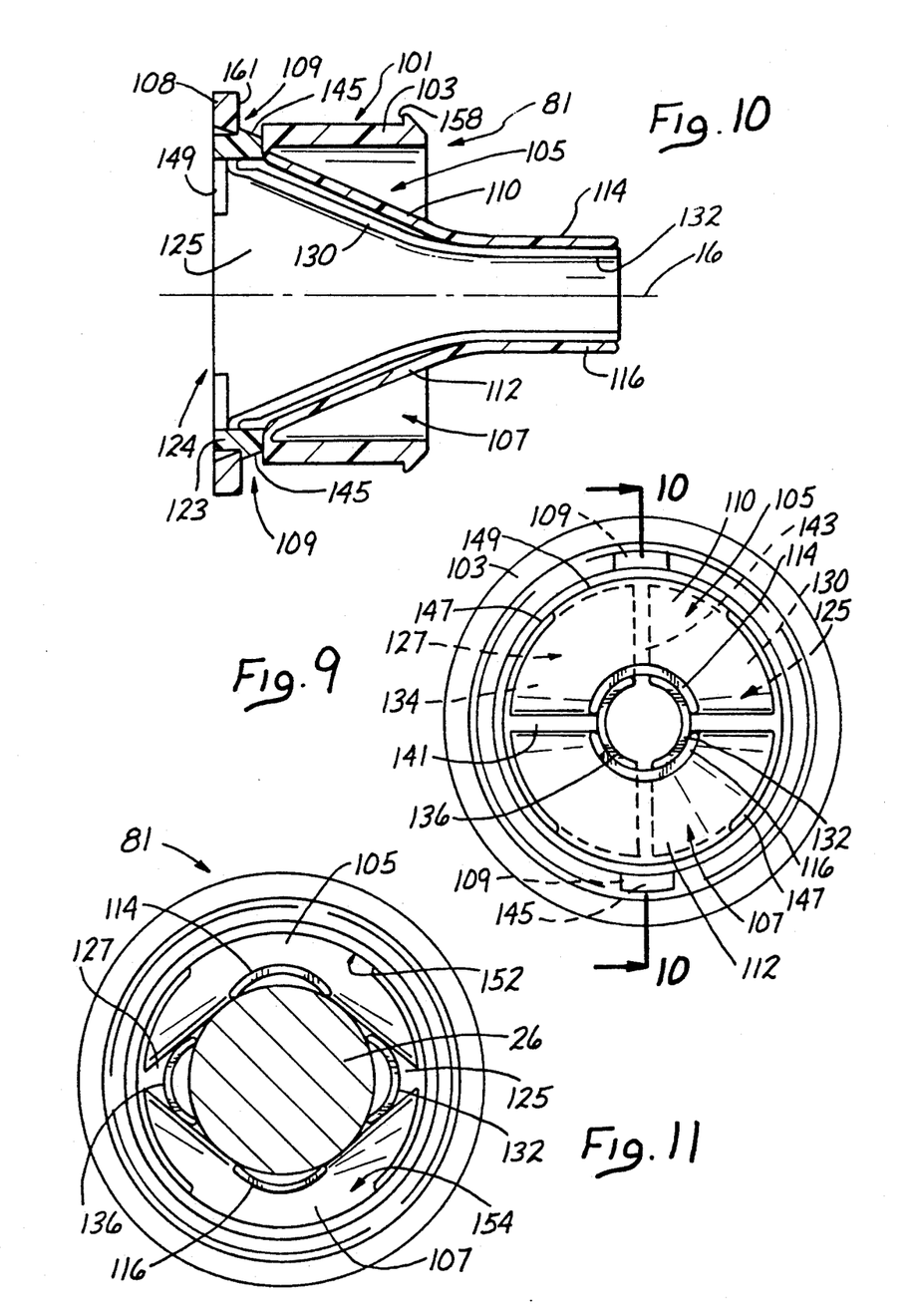
FIG. 9 is an end view of one embodiment of the seal protection mechanism.
FIG. 10 is an axial cross-section view of the seal protection mechanism of FIG. 9.
FIG. 11 is an end view of the seal protection mechanism similar to FIG. 10 but illustrating an instrument extending through the mechanism as illustrated in FIG. 8.

The seal protector 81, which is mounted on the trocar 10 in FIG. 6, is shown in an enlarged isolated view in FIG. 10. This enlarged view illustrates an embodiment, wherein the seal protector 81 is formed in two sections. A distal section 101 has an outer cylinder 103 and a pair of integral outer leaves 105 and 107. The distal section 101 also includes an integral annular flange 108 which extends radially outwardly and defines with the cylinder 103 a pair of windows 109. The outer leaves 105 and 107 include funnel portions 110 and 112, respectively, which extend radially distally inwardly from the cylinder 103. The leaves 105 and 107 also include distal portions 114 and 116, respectfully, which may also have the configuration of a cylinder.

A proximal section 121 of the seal protector 81 also includes an outer cylinder 123 and a pair of integral inner leaves 125 and 127 (FIG. 9). These leaves 125 and 127 are configured similar to the leaves 105 and 107. Thus the inner leaf 125 includes a funnel section 130 and a distal section 132 while the inner leaf 127 includes a funnel section 134 and a distal section 136. These two sections of the seal protector 81, the distal section 101 and the proximal section 121, are intended to be disposed in fixed relationship with the inner leaves 125, 127 disposed inwardly of the outer leaves 105, 107. This fixed relationship between the distal section 101 and the proximal section 121 can be accomplished by bonding alternatively the outer cylinder 123 of the proximal section 121 can be provided with a pair of snap flanges 145 which are configured to seat in the windows 129.

The outer leaves 105 and 107 are separated by a radial slot 141 which permits these leaves to be individually moved in opposite directions as the instrument 26 is inserted. In a similar manner, the inner leaves 125 and 127 are separated by a radial slot 143 which is disposed transverse, perpendicular in a preferred embodiment, to the slot 141.

The seal protector 81 is preferably molded from a strong, tough material. In a particular embodiment, characteristics facilitating formation of a living hinge or a lubricous surface may also be of interest. Based on these considerations, materials such as high density polyethylene, Hytrel (a trademark of DuPont), and Valox (a trademark of General Electric) might be considered. The Valox material was chosen for a preferred embodiment.

Depending on the flexibility of the respective leaves 105, 107, 125, and 127, it may be desirable to extend the respective slots 141 and 143 circumferentially along the line which joins the respective leaf to its associated cylinder 103, 123. In FIG. 9 an extension of the slot 141 is designated by the reference numeral 147; an extension of the slot 143 is designated by the reference numeral 149. With the provision of these circumferential slot extensions 147, 149, the leaves 105, 107 and 125, 127 are free to pivot on the remainder of the circumferential structure which functions as a living hinge.

These living hinges are best illustrated in FIG. 11 and designated by the reference numerals 152 and 154 for the respective leaves 105 and 107. This end view of FIG. 11 also illustrates the configuration of the seal protector 81 with the instrument 26 inserted. The accommodating separation of the respective leaves 105, 107 and 125, 127 is apparent from this view.

The seal protector 81 disclosed in these FIGS. 9–11 is illustrated in FIG. 6 mounted to the proximal end of the trocar 10. As illustrated, the protector 81 is preferably mounted co-axially with the aperture 38 with the leaves 105, 107 and 125, 127 functioning as a funnel to guide the instrument 26 toward the aperture 38. In this location, the protector 81 in a preferred embodiment is movable axially between a proximal position, illustrated in FIG. 6, and a distal position illustrated in FIG. 7. These respective positions are defined by interlocking parts of the protector 81 and the annular flange 76 of the end cap 74.

In one embodiment, the cylinder 103 is provided with an annular snap ring having a proximally facing shoulder 158. The cylinder 108 has a distally facing surface 161. In this case, the protector 81 is preferably mounted with the cylinder 103 disposed in sliding engagement with the annular flange 76. The shoulder 158 and surface 161 are separated an axial distance greater than the axial length of the flange 76. This permits the protector 81 to move axially between the proximal and distal positions. In the proximal position, illustrated in FIG. 6, further proximal movement of the protector 81 is prevented by contact between the shoulder 92 on the flange 76 and the shoulder 158 on the cylinder 103. In the distal position, illustrated in FIG. 7, further distal movement of the protector 81 is prevented by contact between the surface 161 of the flange 108 and the surface 94 of the flange 76.

In operation, the instrument 26 is inserted into the funnel formed by the protector 81. As the instrument contacts the inner leaves 125, 127, it moves the protector 81 to the distal position. In this location, the leaves extend between the pointed points 83 of the instrument 26 and the outer portions 39 of the septum valve 36. In a particular embodiment, the distal sections 114, 116 and 132, 136 may actually contact the proximal side of the septum valve 36 although this is not required by the present invention. Nevertheless, this contact is encouraged as it permits the protector 81 to actually engage the septum valve 36. Then as the instrument 26 is further inserted and the leaves 105, 107 and 125, 127 expand radially outwardly, they will also spread the inner portions 37 of the valve 36, thereby enlarging the aperture 38.

Figure 7:
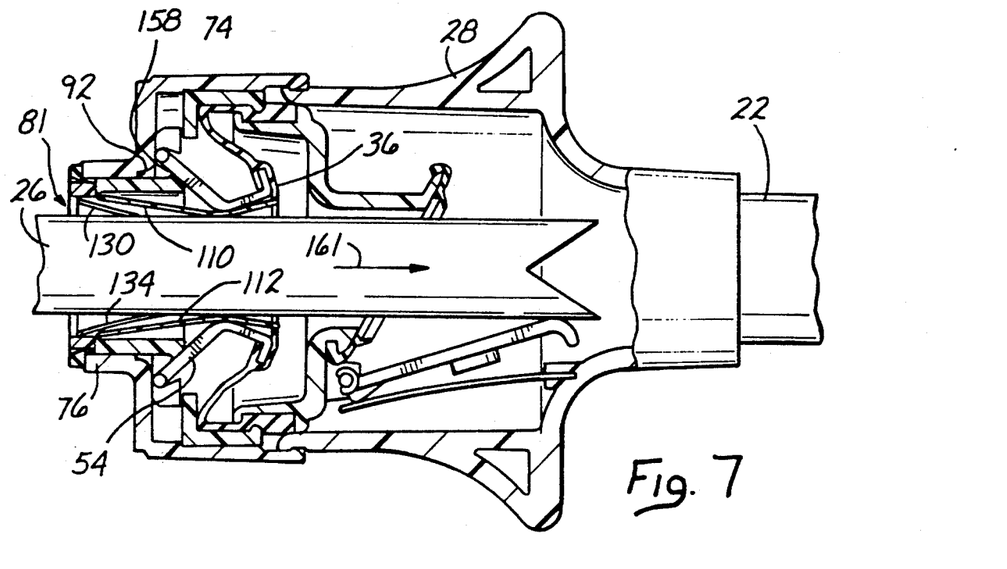
FIG. 7 is an axial cross-section view similar to FIG. 3 illustrating the seal protection mechanism in a distal position as the instrument is being inserted into the trocar.

In the embodiment illustrated in FIG. 7, the distal sections 114, 116 and 132, 136 of the leaves actually extend into the aperture 38 in the distal position. This insures that the aperture 38 is spread at least as far as the leaves of the protector 81. In this case, the protector 81 extends between the instrument 26 and all portions of the septum valve 36.

Once the instrument 26 is in place, it is important that the valve 36 be permitted to engage the outer surface of the instrument in order to form the desired seal and prevent the escape of insufflation gasses. In a particular embodiment, this will require that the seal protector 81 be separated from the septum valve 36 for example by returning the protector 81 to the proximal position.

This movement of the protector 81 from the distal position to the proximal position may occur automatically when the instrument is in place and the protector 81 is no longer subjected to insertion forces. In such an embodiment, the automatic return of the protector 81 would result from the elastomeric forces of the septum valve 36 which compress the leaves 105, 107 and 125, 127 radially inwardly. This compression may result from contact between the valve 36 and the leaves, or contact between the levers 54 and the leaves.

Figure 8:
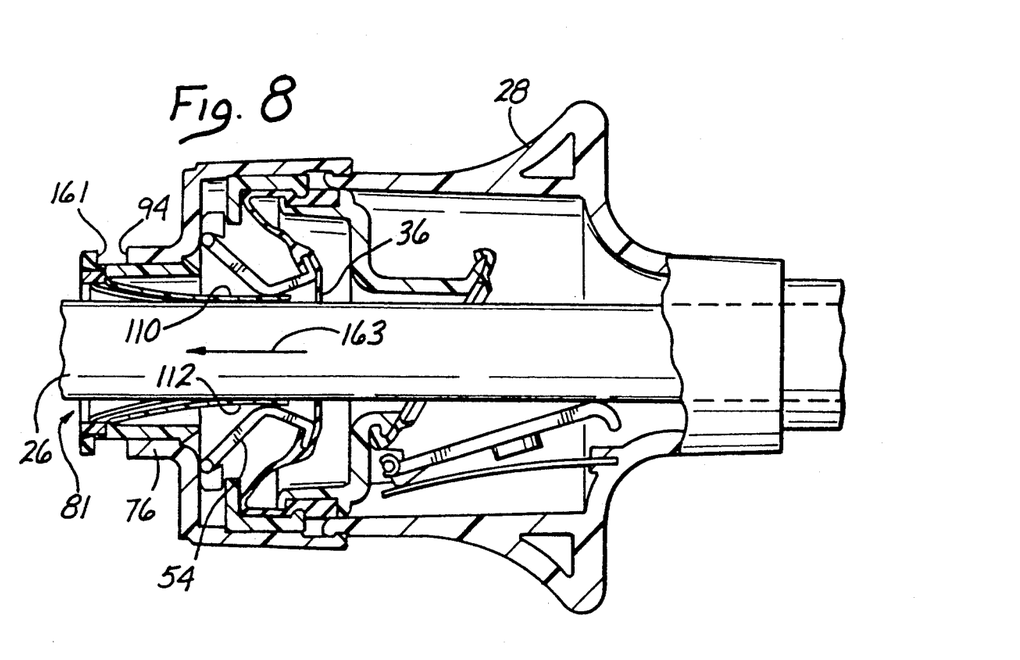
FIG. 8 is an axial cross-section view illustrating the instrument slightly retracted to return the protection mechanism to a proximal position.

In order to facilitate this movement of the protector 81 from the distal position to the proximal position, it may be advantageous to withdraw the instrument 26 slightly to produce a force on the leaves 105, 107 and 125 and 127 in the proximal direction. This movement of the protector 81 to the proximal position is illustrated in FIG. 8 where the feature of automatic retraction is enhanced by the slight movement of the instrument 26 in the direction of arrow 163.

There are many variations on this concept of seal protection which will be apparent to those skilled in the art. Certainly different materials could be used for the protector 81 which could also be formed from more than the two sections 101 and 121. An embodiment including a different number of the leaves 105, 107 and 125, 127 may offer certain advantages in other configurations. It is also particularly advantageous if the protector 81 can protect the valve 36 during insertion of the instrument 26, but also permit the valve 36 to form a seal with the instrument when it has achieved its ultimate position. These features are provided by the axial movement of the protector 81 but this movement may not be required in other embodiments of the invention.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. An access device having an axis extending between a proximal end and an opening distal end, and properties for facilitating introduction into the body of an instrument having a pointed distal tip, the device comprising:
   a housing having walls defining a channel extending through the device;
   a valve disposed in the housing across the channel and adapted to form a seal around the instrument when the instrument is inserted into the channel;
   the valve including inner portions defining an aperture to receive the instrument and outer portions extending radially outwardly of the inner portions;
   means having a continuous, generally conical inner surface engageable by the instrument, and positioned between the instrument and at least the outer portion of the valve for isolating the valve from the pointed distal tip during insertion of the instrument;
   the valve being formed of an elastomeric material; and
   the isolating means being formed of a material having compliance less than that of the elastomeric material forming the valve in order to distribute the insertion forces along the valve.

2. The device recited in claim 1 wherein:
   the isolation means is movable with the instrument between a distal position wherein the isolation means extends between the instrument and at least the outer portion of the valve, and a proximal position removed from the distal position wherein the isolation means is displaced from the valve and the valve is free to form a seal around the instrument.

3. The device recited in claim 2 wherein the isolation means in the distal position is disposed to extend through the aperture in the valve.

4. The device recited in claim 1 wherein the isolation means includes a plurality of leaves overlapping to form an expandable funnel.

5. The device recited in claim 4 wherein the funnel is axially movable with the instrument from a proximal position to a distal position in proximity to the aperture in the valve.

6. The access device recited in claim 1 wherein the isolating means includes:
 a supporting structure carried by the housing;
 a plurality of overlapping leaves defining a generally conical inner surface and pivotal on the supporting structure to accommodate instruments of different diameter.

7. The access device recited in claim 6 wherein the support structure of the isolating means comprises a ring slidable on the housing between a proximal position and a distal position.

8. The access device recited in claim 7 wherein the ring is slidable axially with the instrument between the proximal position and the distal position.

9. An access device having an axis extending between a proximal end and a distal end, and properties for facilitating the introduction into the body of an instrument having a pointed distal tip, the device comprising:
 a housing having walls defining a channel through the device;
 a septum valve disposed in the housing across the channel and adapted to form a seal around the instrument when the instrument is inserted into the channel;
 inner portions of the valve defining an aperture to receive the instrument;
 outer portions of the valve extending radially outwardly of the inner portions; and
 means formed of a generally non-compliant material and disposed between the instrument and at least the outer portion of the valve for funneling the pointed distal tip of the instrument toward the aperture in the septum valve.

10. The device recited in claim 9 wherein the funneling means comprises:
 plurality of leaves forming a funnel having a relatively large proximal end and a relatively narrow distal end extending into proximity with the aperture in the septum valve.

11. The device recited in claim 10 wherein the funnel comprises at least two opposing leaf pairs that are radially offset in overlapping relationship to form a continuous inner surface of the funnel.

12. The device recited in claim 10 wherein the funnel is axially movable with the instrument from a proximal position to a distal position wherein the distal end of the funnel is disposed in proximity with the aperture in the septum valve.

13. The device recited in claim 12 wherein the distal end of the funnel in the distal position extends through the aperture in the septum valve.

14. The device recited in claim 9 wherein:
 the valve has a proximal face;
 the funneling means is movable between a proximal position and a distal position; and
 the funneling means in the distal position contacts the proximal face of the valve to distribute insertion forces across the proximal face of the valve.

15. The access device recited in claim 9 wherein the funneling means includes:
 a supporting structure carried by the housing;
 a plurality of overlapping leaves defining a generally conical inner surface and pivotal on the supporting structure to accommodate instruments of different diameter.

16. The access device recited in claim 15 wherein the supporting structure of the isolating means comprises a ring slidable on the housing between a proximal position and a distal position.

17. The access device recited in claim 16 wherein the ring is slidable axially with the instrument between the proximal position and the distal position.

18. A trocar adapted to facilitate introduction into a body of an instrument having a pointed distal tip, the trocar having an axis extending between a proximal end and a distal end and further comprising:
 a housing having walls defining a channel through the trocar;
 a septum valve disposed in the housing across the channel and adapted to form a seal around the instrument when the instrument is inserted into the channel;
 the valve including lip portions defining a hole to receive the instrument, and outer portions extending radially outwardly of the lip portions;
 means disposed proximally of the valve for prestressing the valve in response to insertion of the instrument into the trocar, the prestressing means enlarging the hole of the valve prior to introduction of the instrument through the valve; and
 means having an expandable inner surface for funneling the prestressed hole to avoid substantial contact between the valve and the instrument as the instrument passes through the hole.

19. The trocar recited in claim 18 wherein the funneling means includes a funnel having an enlarged proximal end and a narrow distal end, the funnel being movable axially between a proximal position and a distal position wherein the distal end of the funnel is disposed in proximity to the valve and concentric with the prestressed hole.

20. The trocar recited in claim 19 wherein the funnel is disposed radially inwardly of the means for prestressing the valve.

21. The trocar recited in claim 19 wherein the funnel comprises a plurality of overlapping leaves providing the inner surface with a generally conical configuration and the funnel is radially expandable to accommodate different diameters of the instrument.

22. The trocar recited in claim 18 wherein the septum valve has a proximal face;
 the insertion of the instrument into the trocar creates insertion forces on the valve; and
 the funneling means is disposed in contact with the proximal face of the valve to distribute the insertion forces across the proximal face of the valve.

23. A trocar assembly having a channel defined along an elongate axis and adapted to receive an instrument having a particular cross-sectional dimension and a sharp distal tip, the trocar assembly comprising:
 an elastomeric septum disposed in said channel and including portions defining an orifice having in a relaxed state a first cross-section area and in an expanded state a second cross-sectional area;
 means responsive to the particular dimension of the instrument for expanding said orifice to the second cross-sectional area; and
 means having a continuous, generally conical inner surface engagable by the instrument and positioned between the instrument and the septum for isolating the septum from the sharp distal tip of the instrument during insertion of the instrument.

24. A seal assembly adapted to receive an elongate object having a sharp distal tip, and to form a seal around the object, the assembly comprising:

a housing including first portions defining a channel extending through the housing and second portions defining a peripheral recess in the housing;

a septum extending across the channel of the housing;

portions of the housing defining a hole adapted to receive the object with the septum portions forming a seal around the object;

actuation means movable within the peripheral recess of the housing for enlarging a hole in response to insertion of the object into the channel; and means having a continuous, generally conical inner surface engagable by the object, and positioned between the instrument and the septum for isolating the septum from the sharp distal tip of the object during insertion of the instrument.

* * * * *

Disclaimer 5,308,336—Charles C. Hart, Hunting Beach; Mark A. Ritchart, Murrieta, both of Calif. SEAL PROTECTION MECHANISM. Patent dated May 3, 1994. Disclaimer filed April 22, 1997, by the assignee, Applied Medical Resources Corp.

The term of this patent shall not extend beyond the expiration date of Pat. No. 5,209,737.
*(Official Gazette, June 17, 1997)*